United States Patent [19]
Unruh et al.

[11] Patent Number: 5,866,725
[45] Date of Patent: Feb. 2, 1999

[54] PROCESS FOR THE PRODUCTION OF N-PROPANOL

[75] Inventors: Jerry D. Unruh; Debra A. Ryan, both of Corpus Christi, Tex.; Shannon L. Dugan, Hutchinson, Kans.

[73] Assignee: Celanese International Corporation, Dallas, Tex.

[21] Appl. No.: 989,144

[22] Filed: Dec. 11, 1997

[51] Int. Cl.$^6$ .................................................. C07C 29/14
[52] U.S. Cl. ........................................... 568/881; 568/882
[58] Field of Search .................................. 568/840, 878, 568/880, 881, 884, 885, 882

[56] References Cited

U.S. PATENT DOCUMENTS 4,263,449  4/1981  Saito et al. ............................... 560/263
4,826,799  5/1989  Cheng et al. ............................. 502/301

*Primary Examiner*—Michael L. Shippen
*Attorney, Agent, or Firm*—M. Susan Spiering

[57] ABSTRACT

A process for the production of purified n-propanol comprising contacting in a hydrogenation zone propionaldehyde and hydrogen with an active porous cobalt catalyst under hydrogenation conditions of temperature and pressure for the production of alcohols from aldehydes, either in the substantial absence of water, or in the presence of water in an amount up to about 3 wt % based on the weight of the liquid hydrogenation reaction product, to produce said reaction product comprising n-propanol, and purifying said reaction product by fractional distillation in the substantial absence of water, or in the presence of water in an amount up to about 3 wt % based on the total weight of feed to the fractionating column.

11 Claims, No Drawings

PROCESS FOR THE PRODUCTION OF N-PROPANOL

BACKGROUND OF THE INVENTION

1. Field of the Invention

This invention relates to an improved process for the production of a purified n-propanol by the hydrogenation of propionaldehyde and the fractional distillation of the resulting crude n-propanol.

2. Background Information Including a Description of Related Art

It is known to produce n-propanol by the hydrogenation of propionaldehyde obtained, for example, by the hydroformylation of ethylene by reaction with carbon monoxide and hydrogen. However, in order to be suitable for various applications, e.g., as a solvent for vegetable oils, waxes, resins, and cellulose esters and ethers in the manufacture of polishing compounds, brake fluids and various propyl compounds, the n-propanol must have a high degree of purity including a specified low level of certain impurities produced by the hydroformylation and hydrogenation reactions. To deal with this problem, the crude n-propanol produced by the hydrogenation reaction must be purified, generally by fractional distillation. When any of conventional catalysts such as Raney nickel is used for the hydrogenation of propionaldehyde to n-propanol, undesirably large amounts of certain impurities tend to be formed in the presence of little or no water as a result of side reactions of the hydrogenation reaction, with two of the more significant impurities being n-propyl propionate (prpr) and di-n-propylether (DPE). To reduce the amounts of such impurities formed as a result of these side reactions, the crude propionaldehyde feed to the hydrogenation reaction when Raney nickel is employed as the hydrogenation catalyst, is adjusted to contain a significant amount of water, e.g., at least about 4.0 wt % and up to about 10 wt %, based on the weight of the feed to the hydrogenation reaction, resulting in approximately the same percentage of water in the crude n-propanol product from the reaction, based on the weight of such product. However, while this amount of water results in decreased production of prpr and DPE by-products from the hydrogenation reaction, it renders the separation of prpr from n-propanol in the fractioning column more difficult despite the prpr boiling point of about 122° C., since a prpr/water azeotrope has a boiling point of about 88° C., giving rise to the presence of liquid prpr above the withdrawal point of purified n-propanol in the column. Moreover, the presence of such a large amount of water in the fractionating column makes the recovery of purified n-propanol from the fractionating column more difficult since n-propanol forms a binary azeotrope with water having a boiling point of about 87° C., and a ternary azeotrope with water and DPE having a boiling a point of about 74° C., which must be withdrawn from the column as streams separate from the stream of purified n-propanol having a boiling point of about 97° C. and must be separately purified. Finally, the presence of a relatively large amount of water results in a substantial expenditure of energy, generally through steam consumption, to vaporize the water present, and may also necessitate a larger purification column than would otherwise be necessary to carry out the purification. In view of this, any change in the process is desirable which results in a decreased amount of water necessary in the reactor and the fractionating column and thus a reduction in energy consumption and possibly the size of the column, without any increase in the amount of prpr present in the product which would ordinarily result from the reduced presence of water in the hydrogenation reaction.

The following prior art references may be considered material to the claimed invention.

U.S. Pat. No. 4,263,449, issued Apr. 21, 1981 to Saito et al., discloses a process for producing alcohols, e.g., propanol, by the hydroformylation of an alkenyl compound, e.g., ethylene, and the hydrogenation of the resulting aldehyde in the presence of a hydrogenation catalyst, e.g., Raney cobalt. Water is added at a ratio of 0.5 to 30 times by weight based on the aldehyde produced by the hydroformylation before the hydrogenation.

U.S. Pat. No. 4,826,799, issued May 2, 1989 to Cheng et al., discloses a process of making catalysts by the Raney process including the steps of pelletizing a Raney process metal alloy, e.g., of cobalt and aluminum, in a matrix of polymer and plasticizer followed by removal of plasticizer or plasticizer and polymer, and the leaching out of the aluminum with caustic. The catalyst may be used to hydrogenate an aldehyde to the corresponding alkanol.

SUMMARY OF THE INVENTION

In accordance with this invention, purified n-propanol is produced by a process comprising contacting in a hydrogenation zone propionaldehyde and hydrogen with an active porous cobalt catalyst, e.g., Raney cobalt, under hydrogenation conditions of temperature and pressure for the production of alcohols from aldehydes, either in the substantial absence of water, or in the presence of water in an amount no more than about 3 wt % based on the weight of the resulting crude n-propanol hydrogenation reaction product, and purifying the reaction product by fractional distillation in the substantial absence of water, or in the presence of water in an amount up to about 3 wt % of water, based on the total weight of crude n-propanol feed to the fractionating column.

The use of an active porous cobalt catalyst in the hydrogenation process surprisingly results in the production of significantly smaller amounts of various impurities, including prpr and DPE, than when a catalyst such as Raney nickel is employed. This allows for the use of a substantially lower amount of water in the fractionating column in which the n-propanol product from the hydrogenation process is purified, since less water is needed to reduce the formation of prpr and DPE during the hydrogenation reaction and the decreased amount of water facilitates the separation of prpr from n-propanol in the column, in view of the fact that a smaller amount of a prpr/water azeotrope forms in the column. This in turn reduces the energy necessary to vaporize the water in the column, and/or may also allow for the use of a smaller column, or higher production of n-propanol with an existing column.

DETAILED DESCRIPTION OF THE INVENTION

The propionaldehyde feed to the process of this invention may be obtained from any source, e.g., the noble metal-phosphine ligand catalyzed hydroformylation of ethylene. If the feed is obtained from the latter process, it is not usually necessary to subject it to extensive purification before utilizing it in the hydrogenation, although such feed is generally treated to remove the phosphine ligand.

The cobalt catalysts suitable for use in the hydrogenation reaction of this invention are prepared by treating an alloy of cobalt and at least one other metal, e.g., aluminum, with a chemical agent, e.g., sodium hydroxide, to extract the other metal from the alloy and obtain the cobalt in a highly porous form. Such active porous cobalt catalysts are known in the art and may be obtained commercially, e.g., from W. R. Grace & Co. under the "Raney" trademark. They may be unsupported or supported, for example, on a porous carrier such as alumina or silica, with the metallic portion containing, for example, at least about 80 wt % of cobalt, and any remaining metals being, for example, aluminum, iron, nickel and/or chromium, with chromium, if present, possibly acting as a promoter for the cobalt. For illustrative purposes only, the unsupported catalysts may have an average particle size of, for example, about 15 to about 60 microns, a specific gravity of, for example, about 6.5 to about 7.5, and a bulk density of, for example, about 14 to 18 lb/gal based on a catalyst slurry weight of about 56% solids in water.

The hydrogenation is generally carried out under hydrogenation conditions for the production of alcohols from aldehydes, e.g., a temperature of about 100° C. to about 160° C., a hydrogen pressure of about 100 to about 700 psig, and a catalyst loading of about 2 to about 20 wt %, preferably about 8 to about 10 wt % based on the weight of the liquid feed. In addition, the liquid feed should contain, for example, either substantially no water, or an amount of water, for example, up to about 3 wt %, preferably about 0.0 to about 1.0 wt %, based on the weight of crude hydrogenation reaction product. Note that the terms "substantial absence of water" or "substantially no water" as used in this specification means that no water is added to the hydrogenation reactor and/or the fractionating column and that the only water present in the reactor and, optionally the column is that formed during the hydrogenation reaction itself and in predecessor reactions e.g. hydroformylation. Such amount may be in the range of about 0.01 to about 0.5 wt % based on the weight of the crude n-propanol effluent from the hydrogenation with no additional water being added.

The hydrogenation reaction may be carried out continuously, semi-continuously or batchwise, preferably with some backmixing during the reaction, e.g., a continuous slurry bed system. A rotating mixing element is not necessary, but if one is utilized, it may operate at a rotation rate of, for example, about 1000 to 2000 rpm. The residence time of the hydrogenation reactants in the reaction zone may be in the range, for example of about 10 to about 120 min. In many instances, the hydrogenation reaction product will contain no more than about 100 ppm of n-propyl propionate (prpr) or 150 ppm of di-n-propyl ether (DPE), each of which is significantly less than the amounts of such impurity usually obtained when the hydrogenation is carried out with a Raney nickel catalyst, even when the crude n-propanol products contains at least 4 wt % of water, other conditions being equal.

As stated, the purification of the crude n-propanol from the hydrogenation zone is carried out by fractional distillation in the substantial absence of water, or in the presence of water in an amount up to about 3 wt % preferably about 0.1 to about 1 wt %, based on the weight of feed to the fractionating column. The amount of water entering the column is generally the same as that in the hyrogenation effluent, although in some instances, it may be desirable to add an additional small amount of water within the foregoing range to the column for its cooling effect. To achieve such a cooling effect, most of the water is circulated within the column by either internal reflux wherein water vapor condenses toward the top of the column and flows back down to where it absorbs heat and is revaporized to start the cycle again, or external reflux wherein water-containing liquid streams are withdrawn from the column, most of the water in the stream is separated from the organics, e.g., by decantation, and the liquid water is returned to a point at the upper portion of the column.

The distillation is preferably carried out at atmospheric pressure, although it is possible to operate at subatmospheric or superatmospheric pressures, if desirable under certain circumstances.

In general, the number of trays in the column and amount of heat transferred to the material being purified in the column are sufficient to produce a liquid stream of purified n-propanol containing at least about 99.9 wt % of n-propanol. Typically, a liquid or vapor stream comprising propionaldehyde which has an atmospheric boiling point of about 48°–49° C., is withdrawn at or near the top of the column; condensed DPE as the uncomplexed compound or a mixture of uncomplexed compound with an azeotrope of DPE with n-propanol and/or with both water and n-propanol, and binary azeotropes of water with n-propanol or prpr, all having boiling points in the range of about 74.8 to about 91° C., are withdrawn from the upper portion of the column at a point or points below that of the propionaldehyde; purified n-propanol having an atmospheric boiling point of about 97.3° C. is withdrawn at a point below that of the withdrawal of the DPE; and the bulk of the prpr having a boiling point of about 122.3° C. is withdrawn with the heavy ends at a point or points below that of the purified n-propanol. However, since prpr forms an azeotrope with water having a boiling point of about 88.9° C., some of the prpr in the feed to the column is vaporized as a complex with water and the vapor rises to the withdrawal point of the purified n-propanol. Depending on the heat profile of the column, some of the prpr may be absorbed by the n-propanol and some of it still complexed with water may rise as a vapor past the withdrawal point of the n-propanol to a point where it is condensed with the low boiling components of the stream being purified. It may then flow downward as reflux to the point of withdrawal of the purified n-propanol where some of it may be absorbed by the n-propanol. These effects are directly correlated with the amount of water in the column, with a greater amount of water causing less efficient separation of prpr from n-propanol and smaller amounts of water resulting in more efficient separation. Since the amounts of prpr, DPE and other impurities in the hydrogenation effluent are substantially lower when a cobalt catalyst is employed rather than a catalyst such as Raney nickel, all other conditions being equal, the amount of water which must be present in the hydrogenation reaction to effect a desired reduction in the formation of such impurities and therefore in the crude n-propanol feed to the column is significantly reduced. Furthermore, the presence of less water in the column results in formation of a smaller amount of condensed azeotrope of n-propanol and water drawn from the column from which the n-propanol must be recovered, further reducing the cost of purification.

The following non-limiting examples further illustrate the invention.

EXAMPLE 1 TO 3

In these examples, a crude propionaldehyde stream obtained from the noble metal-phosphine ligand catalyzed hydroformylation of ethylene was hydrogenated using an unsupported cobalt catalyst sold by the Grace Davison Division of W. R. Grace & Co., as "Raney 2700" with a composition of at least about 93.0 wt % cobalt and no more than 6.0 wt % aluminum, 0.7 wt % iron and 0.8 wt % nickel, an average particle size in the range of about 20 to 50 microns, a specific gravity of about 7 and a bulk density of about 15–17 lbs/gal based on a catalyst slurry weight of 56% solids in water. Prior to hydrogenation, the crude propionaldehyde was untreated. The hydrogenation was carried out continuously in a stirred backmixed reactor at a temperature of about 135°–138° C., a hydrogen pressure of about 400 psig, a feed rate of about 20 grams/minute and a stir rate of about 1750 rpm. The catalyst loading was about 8–10 wt % based on the weight of the liquid reaction mixture in the reactor, the water content of the liquid hydrogenation effluent was limited to that formed in the hydroformylation and hydrogenation reactions, and the flows to and from the reactor were controlled to provide a residence time in the reactor of close to about 40 min.

Samples of crude hydrogenation reaction product were withdrawn after on stream total reaction times of from about 8 to 20 hours and analyzed for weight percent of water by Karl-Fischer titration and for parts per million (ppm) of the following impurities by gas chromatography: light ends including ethylene, propionaldehyde; ($C_3$ aldehyde); benzene; cyclohexane; di-n-propyl ether (DPE); 2-methyl pentanal; toluene; n-propyl propionate (prpr); 2-methyl pentanol, and dipropyl propylal. The crude n-propanol product without any water being added to that already present is then treated by fractional distillation to remove most of the impurities and obtain a purified n-propanol.

The results of the analysis of impurities in the hydrogenated samples withdrawn after various total hydrogenation reaction times up to the time of withdrawal of the sample (Time) during the processes of Example 1 to 3 are shown in the table 1.

TABLE 1

Results of the analysis of impurities.
Reaction Conditions at:
Temp: 135° C., Pressure: 400 psi, $C_3$ Feed Rate: ~20 g/min

| Component | Example 1 | Example 2 | Example 3 |
|---|---|---|---|
| Water (%) | 0.16 | 0.22 | 0.16 |
| Light Ends ppm) | 228 | 316 | 187 |
| $C_3$ Aldehyde (ppm) | 280 | 347 | 175 |
| Propanol (%) | 99.6 | 99.6 | 99.3 |
| Benzene (ppm) | 2.4 | 2.5 | 3.1 |
| Cyclohexane (ppm) | 365 | 161 | 100 |
| Dipropyl Ether (ppm) | 131 | 39 | 27 |
| 2-Methyl Pentanal (ppm) | <1 | <1 | <1 |
| Toluene (ppm) | 9 | 7 | 5 |
| Propyl Propionate (ppm) | 55 | 52 | 47 |
| 2-Methyl Pentenal (ppm) | 5 | 2 | 1 |
| 2-Methyl Pentenol (ppm) | 361 | 287 | 267 |
| Dipropyl Propylal (ppm) | 196 | 158 | 130 |

As shown by the amounts of impurities indicated in the table, the process of Example 1–3 under the invention, utilizing an active porous cobalt hydrogenation catalyst, yielded a crude hydrogenation reaction product containing relatively low amounts of n-propyl propionate (prpr), i.e., well under 100 ppm. These amounts are lower than those produced in the hydrogenation reaction when a conventional Raney nickel hydrogenation catalyst is employed. For this reason it is not necessary to add any water to that already present in the crude propionaldehyde feed to the hydrogenation reaction, which would subsequently be transmitted to the fractionating column, to obtain a purified n-propanol product with a sufficiently low prpr content to meet specifications. Furthermore, the presence of a small amount of water in the column improves the efficiency of recovery of n-propanol since less water/n-propanol azeotrope is formed which must be withdrawn from the column and treated separately to recover pure n-propanol. In contrast, the hydrogenation product of a processing Raney nickel, in view of its much higher content of prpr, requires a significantly larger amount of water in the hydrogenation reaction, e.g., above about 4 wt %, to reduce substantially the amounts of prpr and other impurities formed in the reaction. Furthermore, most of any water added to the Raney nickel catalyzed hydrogenation to reduce the formation of impurities is ultimately transferred to the fractionating column when the crude n-propanol hydrogenation product is purified. Thus, a significantly larger amount of water is inevitably present in the fractionating column when Raney nickel is the catalyst than is necessary when cobalt catalyst is employed. The use of the cobalt catalyst under the invention therefore results in a lower energy cost and/or the necessity for a smaller column due to the presence of less water in the column, and possibly more efficient production of purified n-propanol having less prpr impurity because of the formation of smaller amounts of water/n-propanol and water/prpr binary azeotropes, than when a conventional Raney nickel hydrogenation catalyst is employed.

We claim:

1. A process for the production of purified n-propanol comprising contacting in a hydrogenation zone propionaldehyde and hydrogen with a cobalt catalyst under hydrogenation conditions of temperature and pressure for the production of alcohols from aldehydes, either in the substantial absence of water, or in the presence of water in an amount up to about 3 wt % based on the weight of the liquid hydrogenation reaction product, to produce said reaction product comprising n-propanol, and purifying said reaction product by fractional distillation in the substantial absence of water, or in the presence of water in an amount up to about 3 wt % of water, based on the total weight of feed to the fractionating column.

2. The process of claim 1 wherein said hydrogenation reaction and fractional distillation are carried out in the substantial absence of water.

3. The process of claim 1 wherein said hydrogenation reaction and fractional distillation are carried out in the presence of water in an amount up to about 3 wt % of the liquid hydrogenation reaction product or feed to the fractionating column respectively.

4. The process of claim 1 wherein said hydrogenation reaction product comprises no more than about 100 ppm of n-propyl propionate.

5. The process of claim 1 wherein said propionaldehyde is obtained from the hydroformylation of ethylene.

6. The process of claim 1 wherein the cobalt catalyst contains at least about 80 wt % of cobalt.

7. The process of claim 6 wherein said catalyst is prepared by treating an alloy of cobalt and at least one other metal with a chemical agent to extract the other metal from the alloy and obtain the cobalt in a highly porous form.

8. The process of claim 7 wherein said other metal is aluminum and said treating agent is sodium hydroxide.

9. The process of claim 7 wherein said catalyst is unsupported and has a particle size of about 15 to about 60 microns, a specific gravity of about 6.5 to about 7.5, and a bulk density of about 14 to 18 lb/gal based on a catalyst slurry weight of 56% solids in water.

10. The process of claim 1 wherein said hydrogenation is carried out continuously with at least some backmixing at a temperature of about 100° C. to about 160° C., a hydrogen pressure of about 100 to about 700 psig., and a catalyst loading of about 2 to about 20 wt %, based on the weight of the feed.

11. The process of claim 9 wherein said purified n-propanol contains at least about 99.9 wt % of pure n-propanol.

* * * * *